United States Patent [19]
Lindquist

[11] Patent Number: 5,905,158
[45] Date of Patent: *May 18, 1999

[54] SUNSCREENING COMPOSITIONS COMPRISING NATURAL PRODUCTS OF A MARINE HYDROID, AND DERIVATIVE THEREOF

[76] Inventor: Niels L. Lindquist, 111 Noyes Ave., Morehead City, N.C. 28557

[21] Appl. No.: 08/928,987

[22] Filed: Sep. 12, 1997

Related U.S. Application Data

[62] Division of application No. 08/749,930, Nov. 14, 1996, Pat. No. 5,705,146
[60] Provisional application No. 60/009,147, Nov. 28, 1995.

[51] Int. Cl.$^6$ .................................................. C07D 277/36
[52] U.S. Cl. .............................................................. 548/186
[58] Field of Search ..................................... 548/186, 189

[56] References Cited

U.S. PATENT DOCUMENTS

| | | | |
|---|---|---|---|
| 3,636,077 | 1/1972 | Stauffer | 424/60 |
| 3,751,563 | 8/1973 | Richardson | 560/19 |
| 4,264,581 | 4/1981 | Kerkhof | 424/60 |
| 5,000,946 | 3/1991 | Bird et al. | 424/59 |
| 5,152,983 | 10/1992 | Nambudiry | 424/60 |
| 5,210,275 | 5/1993 | Sabatelli | 560/36 |
| 5,298,647 | 3/1994 | Robert et al. | 560/16 |
| 5,338,539 | 8/1994 | Raspanti | 424/59 |
| 5,352,793 | 10/1994 | Bird et al. | 546/315 |

OTHER PUBLICATIONS

Cativiela and Diaz de Villegas, *Tetrahedron* 49: 497–506 (1993).
Lindquist et al., *Tet. Lett.* 37: 9131–34 (1996).
DeSimone, E.M. II, *Handbook of Nonprescription Drugs*, American Pharmaceutical Association, Washington, D.C. : 619–24 (1996).
Results of a Chemical Abstract search (1995).

*Primary Examiner*—Richard L. Raymond
*Attorney, Agent, or Firm*—Kevin M. Farrell

[57] ABSTRACT

The invention relates to novel UVB/UVA-absorbing chromophores that are present in the natural products of a marine hydroid, and derivatives thereof, useful as sunscreening agents. Furthermore, the present invention relates to methods for protecting skin from the damaging effects of solar ultraviolet radiation. This method comprises topically applying to the skin an effective coating of a sunscreen composition of the present invention. Additional embodiments of the invention use these natural UV-absorbing compounds, or derivative thereof, as additives as a means of providing UV-protective plastics, paints, and waxes.

6 Claims, No Drawings

SUNSCREENING COMPOSITIONS COMPRISING NATURAL PRODUCTS OF A MARINE HYDROID, AND DERIVATIVE THEREOF

This application is a division of application No. 08/749,930, filed Nov. 14, 1996, now U.S. Pat. No. 5,705,146, which claims priority to Provisional patent application No. 60/009,147, filed Nov. 28, 1995.

BACKGROUND

1. Field of Invention

This invention relates to natural ultra-violet absorbing compounds, and derivatives thereof, useful as broadly effective UVB/UVA-screening compounds for topical application to skin, and other surfaces where enhanced UV protection against the damaging effects of sunlight is desired.

2. Description of Prior Art

Solar ultraviolet light is known to cause significant damage to human skin. Excessive exposure to solar UVB (i.e., wavelengths of the solar spectrum from 290 to 320 nm) causes erythema (sunburn), and chronic exposure can increase the risk of developing skin tumors. The UVA region of sunlight (i.e., wavelengths between 320 and 400 nm) penetrates more deeply into the skin than does UVB and was previously thought to have a minimal impact on the skin other than to promote tanning. However, UVA is now known to accelerate skin wrinkling and aging, negatively affect the immune system, and possibly increasing the risk of developing skin cancer. Thus significant effort has been devote toward finding effective means of protecting human skin and other materials from the damaging effects of both the UVB and UVA components of sunlight.

These efforts, by a great number of people, have resulted in the development and patenting of numerous synthetic organic compounds that absorb ultraviolet light, primarily UVB, to protect skin from the damaging effect of sunlight. Most commonly, mixtures of these UV-absorbing compounds are dispersed in lotions, creams, or sprays that are applied topically to the skin.

As early examples: U.S. Pat. No. 4,264,581 to Kerkhof et al. (1981) discloses a sunscreen composition containing a mixture of 2-ethythexyl dimethyl para-amino benzoate and 2-hydroxy-4-methoxy-benzophenone; U.S. Pat. No. 3,751,563 to Richardson (1973) discloses a sunscreen composition containing a mixture 2-ethoxyethyl para-methoxycinnimate, amyl para-dimethylamino benzoate, homo-menthyl salicylate, and 2-hydroxy4-methoxybenophenone; and U.S. Pat. No. 3,636,077 to Stauffer (1972) discloses a sunscreen composition containing salts of 5-benzoyl-4-hydroxy-2-methoxy benzene sulfonic acid and 4-aminobenzoic acids or esters. These pioneering compositions effectively absorbed UVB but have limited abilities to absorb in the UVA region of the solar spectrum.

More recently, efforts have focused on producing effective UVA blockers. One of the first patented UVA blockers to be included in sunscreens was 4-t-butyl4'-methoxydibenzoylmethane, also known as Octyl Methoxy Dibenzoyl Methane (CTFA), available from Givaudan Corporation under the trade name Parsol 1789. Since 1990, an increasing number of U.S. patents have been issued for novel UVA-absorbing compounds—examples include U.S. Pat. No. 5,210,275 to Sabatelli (1993), U.S. Pat. No. 5,298,647 to Robert et al. (1994), and U.S. Pat. No. 5,338,539 to Raspanti (1994).

Commonly, these synthetic compounds absorb most effectively in either the UVB or UVA region. Thus, for a sunscreen composition to be a broadly effective across the entire solar UV spectrum, it must contain a mixture of UVB-absorbing and UVA-absorbing compounds. Sabatelli et al. in U.S. Pat. No. 5,210,275 (1993) attempt to address this issue by synthesizing compounds containing both a UVB- and a UVA-absorbing chromophore. Alternatively, if a single chromophore had a very broad absorption band that was optimally situated within the solar UV spectrum, a compound containing such a chromophore could function as a broadly effective UVB/UVA screen.

Although nearly all UV-blocking compounds currently offered commercially in sunscreening compositions are synthetic materials, the patenting of naturally occurring UV-absorbing compounds is becoming more common. This interest in natural sunscreens is being driven, in part, by consumer preferences which are shifting away from synthetic materials and toward natural substances that can perform the same task with equal or greater efficiency. The diverse sources of novel, natural UV screens include, for example, terrestrial plants [(U.S. Pat. No. 5,152,983 to Nambudiry et al. (1992)] and marine invertebrates [(U.S. Pat. No. 5,352,793 to Bird et al. (1993)]. Several of these natural compounds, however, have significant limitations related to their stability and water solubility that prohibit their use in sunscreening compositions, and in particular "water-resistant" formulations.

OBJECTS AND ADVANTAGES

Notwithstanding the foregoing developments, there remains a continued need to identify new compounds and compositions which are effective for protecting the skin from ultraviolet radiation in both the UVB and UVA regions. It is accordingly the object of the present invention to provide new compounds possessing broad spectrum UV-absorbing properties via novel chromophores which efficiently absorb both UVB and UVA radiation.

These novel chromophores occur in compounds (named the tridentatols) that are produced by the marine hydroid Tridentata margata (Stachowicz and Lindquist 1996, Lindquist et al. 1996). This animal typically grows attached to seaweed floating at the sea surface, and thus is exposed daily to extremely high levels of solar UV. In-depth chemical analysis of this hydroid found that the only compounds it possesses that absorb solar UVB and UVA radiation are the tridentatols.

The sulfur-containing dithio-carbamate functional group of the tridentatol's UV-absorbing chromophores unexpectedly shifts their absorbances into the UVB and UVA regions and significantly broadens their absorptions so that they provide excellent protection against nearly all of solar UV spectrum. Among previously patented UV-screening compounds, only those claimed in U.S. Pat. No. 3,636,077 to Stauffer (1972) have included a sulfur-containing functional group (a sulfonic acid as one substituent on a benzene ring) into the chromophore; however, no previously patented sunscreen has incorporated a dithio-carbamate functional group into the chromophore.

The ability of the tridentatol's UV-absorbing chromophores to broadly absorb both UVB and UVA is illustrated by the wavelenght of maximum absorption for these compounds (typically 320–342 m), their high molar extinction coefficients (i.e., a measure of per molecule UV-absorbing power) of between 10,000 and 25,000, and their broad absorptions. For the tridentatols, the width of their absorption peak at half peak height (HPH) is 65–75 nm.

Although HPH values for currently marketed UVB-screening compounds can approach those of the tridentatols, much of their UV-absorbing potential lies below 290 nm, the lower limit of solar UV reaching the Earth's surface. Thus these compounds are useful UVB screens, but because their UV-absorbing ability rapid declines beyond 320 nm, they are of limited use as broad spectrum UVA screens.

Among the UVA-blocking compounds on the market, their HPH values tend to be lower (e.g., Parsol 1789 discussed hereinbefore has a HPH value of 55 nm) and thus have limited UVB-absorbing power.

Because the hydroid compounds efficiently absorb both UVB and UVA, sunscreening compositions using these compounds, or derivatives thereof, alone, or in combination with other UVB-blocking compounds, would require less material to achieve a desired Sun Protection Factor (SPF) level while providing superior protection against UVA.

The lipophilic (i.e., water-insoluble) characteristics of the tridentatols are similar to synthetic UV-absorbing compounds currently used in "water-proof" sunscreens. Thus, these natural marine compounds, and derivatives thereof, embodied in the invention are appropriate for "water-proof" sunscreen formulations.

Because compounds of the invention can be obtained by extraction of the source organism, the hydroid Tridentata marginata, sunsceeening compositions using hydroid extracts containing tridentatols as the "active" UV-blocking ingredient can be marketed as "natural" or "all natural" according to the composition of the specific formulation. This desirous label can not be used for sunscreen compositions using synthetic UV-absorbing compounds.

Accordingly, I provide a sunscreen composition comprising as an effective component thereof of at least one compound of formula I or formula II

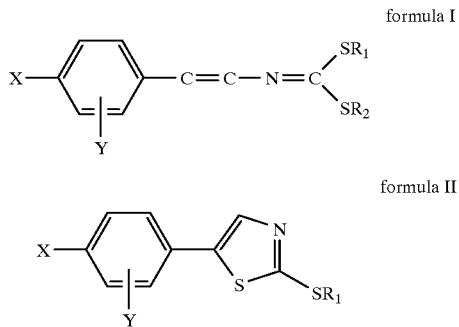

wherein:

R1 and R2 are independently selected from alkyl, branched alkyl, alkenyl, cycloalkenyl, alkoxy, alkenyloxy, alkanoyl, alkylamino, alkenylamino, aryl, substituted aryl, or alkaryl with carbon chain length from 1 to 18 carbons, or any combination of the above X is hydroxy, alkoxy (with the carbon-based chain component of the oxygen substituent selected from the groups described hereinbefore for R1 and R2), amino, alkylamino (with the carbon-based chain component of the nitrogen substituent selected from the groups described hereinbefore for R1 and R2)

Y is hydrogen, hydroxy, alkoxy (with the carbon-based chain component of the oxygen substituent selected from the groups described hereinbefore for R1 and R2), amino, alkylamino (with the carbon-based chain component of the nitrogen substituent selected from the groups described hereinbefore for R1 and R2) and can be either in the ortho or meta position to X and wherein R1 may optionally link together with R2 to form a bridging group within one of the UV-absorbing compounds, or R1 or R2 may optionally link together 2 or more of these UV-absorbing compounds in a cross-linked, polymeric structure.

Additionally R1 or R2 may optionally link together with X or Y to form a bridging group within one of the UV-absorbing compounds, or the R-X or R-Y bridges may optionally that link together 2 or more of these UV-absorbing compounds in a cross-linked, polymeric structure.

Because the types of substituents represented by R1 and R2, hereinbefore described, will have a negligible effect on the UV-absorbing properties of the chromophores contained in compounds of formula I and formula II, the exact nature of these substituents is not critical to the invention's UV-absorbing properties and thus are included as part of the invention because these variations are possible without departing from the present invention's spirit and scope.

Additionally, because the UV-absorbing properties of the invention vary in a predictable manner depending on the forms and the positions of the X and Y substituents on the aromatic ring, any compound of formulae I or II having an oxy- or amino-substituents at the X or Y position will broadly absorb in the UVB and UVA regions and thus are included as part of the invention because these variations also are possible without departing from the present invention's spirit and scope.

Methods of Obtaining Compounds of the Invention:

The compounds of formula I and formula II may be obtained from the marine hydroid Tridentata marginata, by extraction of fresh, frozen, or dried hydroid tissue using procedures described by, but not limited to, Stachowicz and Lindquist (1996).

In summary, the hydroid tissue is extracted using a lipid-solublilizing organic solvent, or solvent mixture, for example, but not limited to, a 2:1 V/V mixture (V/V) of dichloromethane- and methanol. After exhaustive extraction with said solvents, the crude extract is concentrated by rotary evaporation. The reduced extract is then partitioned between water and preferably ethyl acetate, but other water-immiscible organic solvents could also be used for this partition step. After separating the ethyl acetate and water layers, the ethyl acetate soluble material is rotary evaporated to an oily residue and the water fraction discarded.

The lipid-soluble material is then fractionated using silica-gel flash chromatography. The initial fraction is eluted with a nonpolar solvent such as hexane or iso-octane. Solvent mixtures having an increasing proportion of diethyl ether or ethyl acetate in hexane are used to sequentially elute the tridentatols.

Final purification of the tridentatols is achieved by silica high-performance liquid chromatography, using, for example, an 8.5% mixture of ethyl acetate in iso-octane as the eluting solvent. Elution of compounds of formula I and formula II is detected using a UV detector or photo-diode array detector. The above extraction and purification procedure for the tridentatols is provided only as a preferable example, and is not limiting as the only extraction and purification scheme.

Alternatively, compounds of formula I and formula II may be synthesized from simple precursors, but in no way limited to the following example. The compound 2-(4-hydroxyphenyl)-ethlyenamine could be converted to the methoxylated derivative of the natural products by facile and high yielding procedures described by Cativiela and Diaz de Villegas (1993). Reaction of 2-(4hydroxyphenyl)-ethylenamine with carbon disulfide and methyl iodide in the presence of tri-ethylamine in chloroform, and the subsequent reaction with methyl iodide in the presence of potassium carbonate should afford a high yield of methoxy tridentatols.

Preparing a topical sunscreen:

In a further embodiment of the invention, there is provided a means of screening skin from ultraviolet radiation, the method comprises applying to the skin a physiologically acceptable composition containing at least one compound of formula I and/or formula II as hereinbefore described.

In a specific example of a composition applied to human skin, at least one compound of formulae I or II is combined with a water-insoluble mixture such a as paraffin oil to give an oil phase that is combined with an aqueous phase to form an oil-in-water emulsion in the presence of a suitable emulsifier (e.g., ethoxylated fatty acids, ethoxylated esters, ethoxylated fatty ethers, ethoxylated alcohols, phosphated esters, fatty acid amides, acyl lactylates, and fatty alcohols). Examples of suitable carriers may include oils, paraffin, squalene, and octyl palmetate, and oil/alcohol mixtures.

The temperature at which the composition is formed is not critical and may be selected in accordance with the nature of the components thereof.

Further components such as perfumes, coloring agents, antioxidants (e.g., BHA, BHT, ascorbates, tocopherols), oxygen scavengers, and other materials that enhance the appearance of the composition may be used in the composition of the present invention. Examples of oxygen scavengers include compounds that in the presence of oxygen are oxidized more readily than the compounds of formulae I or II. An example of an oxygen scavenger is sodium thiosulphate.

The composition may contain additives making the composition useful as a cosmetic or pharmaceutical.

One or more compounds of formula I and/or formula II may be utilized in the composition of the present invention and generally the concentration of said compound(s) is in the range of 0.1% to 20% by weight of the total composition. However, higher or lower concentrations of the compounds may be used depending on the required degree of sunscreening.

SUMMARY, RAMIFICATIONS, AND SCOPE

This invention provides compounds containing novel UVB-/UVA-absorbing chromophores present in the natural products of a marine hydroid, and structural derivatives thereof that do not significantly alter the UV-absorbing properties of the chromophores. The compounds of the invention broadly absorb both UVB and UVA radiation so that a single compound of the invention can provide a level of protection against solar UV that previously would require formulating a composition containing both UVB-absorbing and UVA-absorbing compounds. Because the compounds of the invention are not soluble in water, they may be used in "water-resistant" sunscreen formulations. Because compounds of the invention can be extracted from a marine hydroid, the term "natural" can be used to market a sunscreen formulation containing lipophilic extracts of the hydroid. The preferred embodiment of the invention is the incorporation of one or more of the compounds of the invention, preferably as 0.1% to 20% of the formulation, into a physiologically suitable composition for topical application to skin to prevent erythema and other damaging effects of exposure to solar ultra-violet light.

Because the types of substituents represented by R1 and R2, hereinbefore described, will have a negligible effect on the UV-absorbing properties of the chromophores contained in compounds of formulae I and II, the exact nature of these substituents is not critical to the invention's UV-absorbing properties and thus are included as part of the invention because these variations are possible without departing from the present invention's spirit and scope.

Additionally, because the UV-absorbing properties of the invention vary in a predictable manner depending on the forms and the positions of the X and Y substituents on the aromatic ring, any compound of formulae I or II having an oxy- or amino-substituents at the X or Y position will broadly absorb in the UVB and UVA regions and thus are included as part of the invention because these variations also are possible without departing from the present invention's spirit and scope.

Thus the scope of the invention should be determined by the appended claims and their legal equivalents, rather than by the examples given.

Additional embodiments of the invention use these natural UV-absorbing compounds, or derivative thereof in, or on, other materials where UV protection is desired, for example, but not limited to, plastics, paints, and waxes.

I claim:

1. An isolated compound comprising:

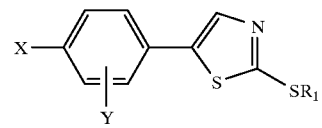

Formula II wherein:

$R_1$ is selected from the group consisting of alkyl, alkenyl, alkoxy, alkenyloxy, alkanoyl, alkylamino, alkenylamino, and alkaryl, with a carbon chain length of from 1 to 18 carbons for substituents other than hydrogen;

X is —$OR_2$ where $R_2$ is selected from the group consisting of hydrogen, alkyl, alkenyl, alkoxy, alkenyloxy, alkanoyl, alkylamino, alkenylamino, and alkaryl, with a carbon chain length of from 1 to 18 carbons for substituents other than hydrogen; or X is —$NHR_2$ where $R_2$ is selected from the group consisting of hydrogen, alkyl, alkenyl, alkoxy, alkenyloxy, alkanoyl, alkylamino, alkenylamino, and alkaryl, with a carbon chain length from 1 to 18 carbons for substituents other than hydrogen;

Y is –$OR_3$ wherein $R_3$ is selected from the group consisting of hydrogen, alkyl, alkenyl, alkoxy, alkenyloxy, alkanoyl, alkylamino, alkenylamino, and alkaryl, with carbon chain length from 1 to 18 carbons for substituents other than hydrogen; or Y is —$NHR_3$ where $R_3$ is selected from the group consisting of hydrogen, alkyl, alkenyl, alkoxy, alkenyloxy, alkanoyl, alkylamino, alkenylamino, and alkaryl, with a carbon chain length from 1 to 18 carbons for substituents other than hydrogen;

Y is hydrogen; or $R_1$ can form an intra-molecular bond with X or Y to form a bridging group within the UV-absorbing compound, or $R_1$ can form an inter-molecular bond thereby linking the compound of formula II with other UVB- or UVA-absorbing compounds.

2. The isolated compound of claim 1 wherein $R_1$ forms an intra-molecular bond with X or Y to form a bridging group within the UV-absorbing compound.

3. The isolated compound of claim 1 wherein $R_1$ forms an inter-molecular bond with X or Y thereby linking two or more of the UV-absorbing compounds of formula II in a cross-linked, polymeric structure.

4. The isolated compound of claim 1 wherein $R_1$ forms an inter-molecular bond thereby linking the compound of formula II with other UVB- or UVA-absorbing compounds.

5. The isolated compound of claim 1 wherein $R_1$ is —$CH_3$, X is —OH, and Y is —H.

6. The isolated compound of claim 1 wherein $R_1$ is —$CH_3$, X is —$OCH_3$, and Y is —H.

* * * * *